United States Patent
Rende et al.

(10) Patent No.: US 6,756,515 B2
(45) Date of Patent: *Jun. 29, 2004

(54) DEHYDROGENATION PROCESS USING LAYERED CATALYST COMPOSITION

(75) Inventors: Dean E. Rende, Cary, IL (US); Andrew W. Broerman, Des Plaines, IL (US); Andrea G. Bozzano, Des Plaines, IL (US); R. Joe Lawson, Arlington Heights, IL (US); Karl Z. Steigleder, Glen Ellyn, IL (US); Masao Takayama, Isehara (JP)

(73) Assignee: UOP LLC, Des Plaines, IL (US)

( * ) Notice: Subject to any disclaimer, the term of this patent is extended or adjusted under 35 U.S.C. 154(b) by 54 days.

This patent is subject to a terminal disclaimer.

(21) Appl. No.: 10/281,420

(22) Filed: Oct. 25, 2002

(65) Prior Publication Data

US 2003/0105373 A1 Jun. 5, 2003

Related U.S. Application Data

(63) Continuation-in-part of application No. 09/887,229, filed on Jun. 22, 2001, now Pat. No. 6,486,370.

(51) Int. Cl.$^7$ .......................... C07C 5/32; C07C 5/327; C07C 5/333

(52) U.S. Cl. ................. 585/444; 585/374; 585/624; 585/660

(58) Field of Search ................. 585/374, 444, 585/629, 660

(56) References Cited

U.S. PATENT DOCUMENTS

| 6,177,381 B1 | 1/2001 | Jensen et al. | 502/325 |
| 6,280,608 B1 | 8/2001 | Jensen et al. | 208/143 |

*Primary Examiner*—Thuan D Dang
(74) *Attorney, Agent, or Firm*—John G. Tolomei; Michael A. Moore

(57) ABSTRACT

This invention relates to a dehydrogenation process using a layered catalyst composition. The catalyst composition comprises an inner core such as alpha-alumina, and an outer layer bonded to the inner core composed of an outer refractory inorganic oxide such as gamma-alumina. The outer layer has uniformly dispersed thereon a platinum group metal such as platinum and a promoter metal such as tin. The composition also contains a modifier metal such as lithium. The catalyst composition shows improved durability and selectivity for dehydrogenating hydrocarbons, especially at dehydrogenation conditions comprising a low water concentration.

18 Claims, No Drawings

DEHYDROGENATION PROCESS USING LAYERED CATALYST COMPOSITION

CROSS REFERENCE TO RELATED APPLICATION

This application is a continuation-in-part of prior U.S. application Ser. No. 09/887,229, filed Jun. 22, 2001 now U.S. Pat. No. 6,486,370, which is incorporated herein by reference in its entirety.

FIELD OF THE INVENTION

This invention relates to a hydrocarbon dehydrogenation process using a layered catalyst composition at select operating conditions for increased catalyst stability.

BACKGROUND OF THE INVENTION

Platinum based catalysts are used for numerous hydrocarbon conversion processes. In many applications promoters and modifiers are also used. One such hydrocarbon conversion process is the dehydrogenation of hydrocarbons, particularly alkanes such as isobutane which are converted to isobutylene. For example, U.S. Pat. No. 3,878,131 (and related U.S. Pat. Nos. 3,632,503 and 3,755,481) discloses a catalyst comprising a platinum metal, a tin oxide component and a germanium oxide component. All components are uniformly dispersed throughout the alumina support. U.S. Pat. No. 3,761,531 (and related U.S. Pat. No. 3,682,838) discloses a catalytic composite comprising a platinum group component, a Group IVA (IUPAC 14) metallic component, e.g., germanium, a Group VA (IUPAC 15) metallic component, e.g., arsenic, antimony, and an alkali or alkaline earth component all dispersed on an alumina carrier material. Again all the components are evenly distributed on the carrier.

U.S. Pat. No. 6,177,381 describes a dehydrogenation process using a layered catalyst composition. Example 7 of U.S. Pat. No. 6,177,381 describes testing of Catalysts A, B, E, and F for dehydrogenation activity using a hydrocarbon feed. A water concentration of 2000 ppm based on hydrocarbon weight was injected. The deactivation rates of Catalysts A, B, E, and F were 0.052, 0.032, 0.050, and 0.033° F./hr, respectively.

Although these deactivation rates are relatively low, other dehydrogenation processes are sought that have even lower deactivation rates.

SUMMARY OF THE INVENTION

An improved dehydrogenation process using a layered catalyst composition which exhibits excellent stability at a critical combination of catalyst properties and operating conditions is disclosed. When the thickness of the outer layer of the layered catalyst is in the range of from 40 to 150 microns, the loading of the platinum group metal in the entire layered catalyst is in the range of from about 5 to about 30 gram-mole of the platinum group metal per cubic meter of the entire layered catalyst, and the concentration of the platinum group metal in the outer layer of the layered catalyst is from about 0.026 to about 0.26 gram-mole of the platinum group metal per kilogram of the outer layer, then excellent stability results, provided that the amount of water passed to the layered catalyst is less than 1000 wt-ppm, and preferably less than 300 wt-ppm, and more preferably less than 60 wt-ppm based on the amount of hydrocarbon passed to the layered catalyst. This result was unexpected because previously it had been thought that such high amounts of platinum-group metal in the outer layer would adversely affect stability. However, it is now recognized that even dehydrogenation processes using catalysts that have relatively high amounts of platinum-group metal in the outer layer can be operated at low water concentrations and thus achieve excellent catalyst stability.

In addition, the process disclosed exhibits better selectivity than processes of the prior art, in terms of total selectivity to normal olefins.

In a broad embodiment, this invention is a hydrocarbon dehydrogenation process comprising contacting a hydrocarbon stream with a layered composition under dehydrogenation conditions to give a dehydrogenated product. The layered composition comprises an inner core and an outer layer bonded to the inner core. The outer layer comprises an outer refractory inorganic oxide and has a thickness of from about 40 to about 150 microns. The outer layer also has, uniformly dispersed thereon, at least one platinum group metal and at least one promoter metal, where the concentration of the at least one platinum group metal in the outer layer is from about 0.026 to about 0.26 gram-mole of the platinum group metal on an elemental basis per kilogram of the outer layer. The layered composition has a loading of the at least one platinum group metal of from about 5 to about 30 gram-mole of the platinum group metal on an elemental basis per cubic meter of the layered composition. The layered composition further has dispersed thereon at least one modifier metal. The inner core and the outer refractory inorganic oxide comprise different materials. The dehydrogenation conditions comprise a weight of water passed to the layered composition based on the hydrocarbon weight passed to the layered composition of less than 1000 ppm.

Other objects and embodiments are described in the detailed description of the invention.

INFORMATION DISCLOSURE

U.S. Pat. No. 6,177,381 describes a dehydrogenation process using a layered catalyst composition. The entire teachings of U.S. Pat. No. 6,177,381 are incorporated herein by reference.

DETAILED DESCRIPTION OF THE INVENTION

The present invention relates to a dehydrogenation process that uses layered catalyst composition. The layered catalyst composition comprises an inner core composed of a material which has substantially lower adsorptive capacity for catalytic metal precursors, relative to the outer layer. Some of the inner core materials are also not substantially penetrated by liquids, e.g., metals including but not limited to aluminum, titanium and zirconium. Examples of the inner core material include, but are not limited to, refractory inorganic oxides, silicon carbide and metals. Examples of refractory inorganic oxides include without limitation alpha alumina, theta alumina, cordierite, zirconia, titania and mixtures thereof. A preferred inorganic oxide is alpha alumina.

These materials which form the inner core can be formed into a variety of shapes such as pellets, extrudates, spheres or irregularly shaped particles although not all materials can be formed into each shape. Preparation of the inner core can be done by means known in the art such as oil dropping, pressure molding, metal forming, pelletizing, granulation, extrusion, rolling methods and marumerizing. A spherical inner core is preferred. The inner core whether spherical or not has an effective diameter of about 0.05 mm to about 5 mm and preferably from about 0.8 mm to about 3 mm. For a non-spherical inner core, effective diameter is defined as the diameter the shaped article would have if it were molded into a sphere. Once the inner core is prepared, it is calcined at a temperature of about 400° C. to about 1500° C.

The inner core is now coated with a layer of a refractory inorganic oxide which is different from the inorganic oxide which may be used as the inner core and will be referred to as the outer refractory inorganic oxide. This outer refractory oxide is one which has good porosity, has a surface area of at least 50 $m^2/g$, and preferably at least 150 $m^2/g$, an apparent bulk density of about 0.2 g/ml to about 1.0 g/ml and is chosen from the group consisting of gamma alumina, delta alumina, eta alumina, theta alumina, silica/alumina, zeolites, non-zeolitic molecular sieves (NZMS), titania, zirconia and mixtures thereof. It should be pointed out that silica/alumina is not a physical mixture of silica and alumina but means an acidic and amorphous material that has been cogelled or coprecipitated. This term is well known in the art, see e.g., U.S. Pat. Nos. 3,909,450; 3,274,124; and 4,988,659, all of which are incorporated by reference. Examples of zeolites include, but are not limited to, zeolite Y, zeolite X, zeolite L, zeolite beta, ferrierite, MFI, mordenite and erionite. Non-zeolitic molecular sieves (NZMS) are those molecular sieves which contain elements other than aluminum and silicon and include silicoaluminophosphates (SAPOs) described in U.S. Pat. No. 4,440,871, ELAPOs described in U.S. Pat. No. 4,793,984, MeAPOs described in U.S. Pat. No. 4,567,029 all of which are incorporated by reference. Preferred refractory inorganic oxides are gamma and eta alumina.

A preferred way of preparing a gamma alumina is by the well-known oil drop method which is described in U.S. Pat. No. 2,620,314 which is incorporated by reference. The oil drop method comprises forming an aluminum hydrosol by any of the techniques taught in the art and preferably by reacting aluminum metal with hydrochloric acid; combining the hydrosol with a suitable gelling agent, e.g., hexamethylenetetraamine; and dropping the resultant mixture into an oil bath maintained at elevated temperatures (about 93° C.). The droplets of the mixture remain in the oil bath until they set and form hydrogel spheres. The spheres are then continuously withdrawn from the oil bath and typically subjected to specific aging and drying treatments in oil and ammoniacal solutions to further improve their physical characteristics. The resulting aged and gelled spheres are then washed and dried at a relatively low temperature of about 80° C. to 260° C. and then calcined at a temperature of about 455° C. to 705° C. for a period of about 1 to about 20 hours. This treatment effects conversion of the hydrogel to the corresponding crystalline gamma alumina.

The layer is applied by forming a slurry of the outer refractory oxide and then coating the inner core with the slurry by means well known in the art. Slurries of inorganic oxides can be prepared by means well known in the art which usually involve the use of a peptizing agent. For example, any of the transitional aluminas can be mixed with water and an acid such as nitric, hydrochloric, or sulfuric to give a slurry. Alternatively, an aluminum sol can be made by for example, dissolving aluminum metal in hydrochloric acid and then mixing the aluminum sol with the alumina powder.

It is also required that the slurry contain an organic bonding agent which aids in the adhesion of the layer material to the inner core. Examples of this organic bonding agent include but are not limited to polyvinyl alcohol (PVA), hydroxy propyl cellulose, methyl cellulose and carboxy methyl cellulose. The amount of organic bonding agent which is added to the slurry will vary considerably from about 0.1 wt-% to about 3 wt-% of the slurry. How strongly the outer layer is bonded to the inner core can be measured by the amount of layer material lost during an attrition test, i.e., attrition loss. Loss of the second refractory oxide by attrition is measured by agitating the catalyst, collecting the fines and calculating an attrition loss. It has been found that by using an organic bonding agent as described above, the attrition loss is less than about 10 wt-% of the outer layer. Finally, the thickness of the outer layer varies from about 40 to about 150 microns. One micron equals $10^6$ meter.

Depending on the particle size of the outer refractory inorganic oxide, it may be necessary to mill the slurry in order to reduce the particle size and simultaneously give a narrower particle size distribution. This can be done by means known in the art such as ball milling for times of about 30 minutes to about 5 hours and preferably from about 1.5 to about 3 hours. It has been found that using a slurry with a narrow particle size distribution improves the bonding of the outer layer to the inner core.

Without wishing to be bound by any particular theory, it appears that bonding agents such as PVA aid in making an interlocking bond between the outer layer material and the inner core. Whether this occurs by the PVA reducing the surface tension of the core or by some other mechanism is not clear. What is clear is that a considerable reduction in loss of the outer layer by attrition is observed.

The slurry may also contain an inorganic bonding agent selected from an alumina bonding agent, a silica bonding agent or mixtures thereof. Examples of silica bonding agents include silica sol and silica gel, while examples of alumina bonding agents include alumina sol, boehmite and aluminum nitrate. The inorganic bonding agents are converted to alumina or silica in the finished composition. The amount of inorganic bonding agent varies from about 2 to about 15 wt-% as the oxide, and based on the weight of the slurry.

Coating of the inner core with the slurry can be accomplished by means such as rolling, dipping, spraying, etc. One preferred technique involves using a fixed fluidized bed of inner core particles and spraying the slurry into the bed to coat the particles evenly. The thickness of the layer can vary considerably, but usually is from about 40 to about 150 microns. It should be pointed out that the optimum layer thickness depends on the choice of the outer refractory oxide. Once the inner core is coated with the layer of outer refractory inorganic oxide, the resultant layered support is dried at a temperature of about 100° C. to about 320° C. for a time of about 1 to about 24 hours and then calcined at a temperature of about 400° C. to about 900° C. for a time of about 0.5 to about 10 hours to effectively bond the outer layer to the inner core and provide a layered catalyst support. Of course, the drying and calcining steps can be combined into one step.

When the inner core is composed of a refractory inorganic oxide (inner refractory oxide), it is necessary that the outer refractory inorganic oxide be different from the inner refractory oxide. Additionally, it is required that the inner refractory inorganic oxide have a substantially lower adsorptive capacity for catalytic metal precursors relative to the outer refractory inorganic oxide.

Having obtained the layered catalyst support, catalytic metals can be dispersed on the layered support by means known in the art. Thus, a platinum group metal, a promoter metal and a modifier metal can be dispersed on the outer layer. The platinum group metals include platinum, palladium, rhodium, iridium, ruthenium and osmium. Promoter metals are selected from the group consisting of tin, germanium, rhenium, gallium, bismuth, lead, indium, cerium, zinc and mixtures thereof, while modifier metals are selected from the group consisting of alkali metals, alkaline earth metals and mixtures thereof.

These catalytic metal components can be deposited on the layered support in any suitable manner known in the art. One method involves impregnating the layered support with a solution (preferably aqueous) of a decomposable compound of the metal or metals. By decomposable is meant that upon heating the metal compound is converted to the metal or metal oxide with the release of byproducts. Illustrative of the decomposable compounds of the platinum group metals are chloroplatinic acid, ammonium chloroplatinate, bromoplatinic acid, dinitrodiamino platinum, sodium tetranitroplatinate, rhodium trichoride, hexa-amminerhodium chloride, rhodium carbonylchloride, sodium hexanitrorhodate, chloropalladic acid, palladium chloride, palladium nitrate, diamminepalladium hydroxide, tetraamminepalladium chloride, hexachloroiridate (IV) acid, hexachloroiridate (III) acid, ammonium hexachloroiridate (III), ammonium aquohexachloroiridate (IV), ruthenium tetrachloride, hexachlororuthenate, hexa-ammineruthenium chloride, osmium trichloride and ammonium osmium chloride. Illustrative of the decomposable promoter metal compounds are the halide salts of the promoter metals. A preferred promoter is tin and preferred decomposable compounds are stannous chloride or stannic chloride.

The alkali and alkaline earth metals which can be used as modifier metals in the practice of this invention include lithium, sodium, potassium, cesium, rubidium, beryllium, magnesium, calcium, strontium and barium. Preferred modifier metals are lithium, potassium, sodium and cesium with lithium and sodium being especially preferred. Illustrative of the decomposable compounds of the alkali and alkaline earth metals are the halide, nitrate, carbonate or hydroxide compounds, e.g., potassium hydroxide, lithium nitrate.

All three types of metals can be impregnated using one common solution or they can be sequentially impregnated in any order, but not necessarily with equivalent results. A preferred impregnation procedure involves the use of a steam-jacketed rotary dryer. The support is immersed in the impregnating solution containing the desired metal compound contained in the dryer and the support is tumbled therein by the rotating motion of the dryer. Evaporation of the solution in contact with the tumbling support is expedited by applying steam to the dryer jacket. The resultant composite is allowed to dry under ambient temperature conditions, or dried at a temperature of about 80° C. to about 350° C., followed by calcination at a temperature of about 200° C. to about 700° C. for a time of about 1 to about 4 hours, thereby converting the metal compound to the metal or metal oxide. It should be pointed out that for the platinum group metal compound, it is preferred to carry out the calcination at a temperature of about 400° C. to about 700° C.

In one method of preparation, the promoter metal is first deposited onto the layered support and calcined as described above and then the modifier metal and platinum group metal are simultaneously dispersed onto the layered support by using an aqueous solution which contains a compound of the modifier metal and a compound of the platinum group metal. The support is impregnated with the solution as described above and then calcined at a temperature of about 400° C. to about 700° C. for a time of about 1 to about 4 hours.

An alternative method of preparation involves adding one or more of the metal components to the outer refractory oxide prior to applying it as a layer onto the inner core. For example, a decomposable salt of the promoter metal, e.g., tin (IV) chloride can be added to a slurry composed of gamma alumina and aluminum sol. Further, either the modifier metal or the platinum group metal or both can be added to the slurry. Thus, in one method, all three catalytic metals are deposited onto the outer refractory oxide prior to depositing the second refractory oxide as a layer onto the inner core. Again, the three types of catalytic metals can be deposited onto the outer refractory oxide powder in any order although not necessarily with equivalent results.

Another method of preparation involves first impregnating the promoter metal onto the outer refractory oxide and calcining as described above. Next, a slurry is prepared (as described above) using the outer refractory oxide containing the promoter metal and applied to the inner core by means described above. Finally, the modifier metal and platinum group metal are simultaneously impregnated onto the layered composition which contains the promoter metal and calcined as described above to give the desired layered catalyst.

As a final step in the preparation of the layered catalyst composition, the catalyst composition is reduced under hydrogen or other reducing atmosphere in order to ensure that the platinum group metal component is in the metallic state (zero valent). Reduction is carried out at a temperature of about 100° C. to about 650° C. for a time of about 0.5 to about 10 hours in a reducing environment, preferably dry hydrogen. The state of the promoter and modifier metals can be metallic (zero valent), metal oxide or metal oxychloride.

The layered catalyst composition can also contain a halogen component which can be fluorine, chlorine, bromine, iodine or mixtures thereof with chlorine and bromine preferred. This halogen component is present in an amount of 0.03 to about 1.5 wt-% with respect to the weight of the entire catalyst composition. The halogen component can be applied by means well known in the art and can be done at any point during the preparation of the catalyst composition although not necessarily with equivalent results. It is preferred to add the halogen component after all the catalytic components have been added either before or after treatment with hydrogen.

Although in the preferred embodiments all three metals are uniformly distributed throughout the outer layer of outer refractory oxide and substantially present only in the outer layer, it is also within the bounds of this invention that the modifier metal can be present both in the outer layer and the inner core. This is owing to the fact that the modifier metal can migrate to the inner core, when the core is other than a metallic core.

Although the concentration of each metal component can vary substantially, it is desirable that the platinum group metal be present in a concentration of about 0.01 to about 5 weight percent on an elemental basis of the entire weight of the catalyst and preferably from about 0.05 to about 2.0 wt-%. The promoter metal is present in an amount from about 0.05 to about 10 wt-% of the entire catalyst while the modifier metal is present in an amount from about 0.1 to about 5 wt-% of the entire catalyst. Finally, the atomic ratio of the platinum group metal to promoter metal varies from about 0.05 to about 5. In particular when the promoter metal is tin, the atomic ratio is from about 0.1:1 to about 5:1 and preferably from about 0.5:1 to about 3:1. When the promoter metal is germanium the ratio is from about 0.25:1 to about 5:1 and when the promoter metal is rhenium, the ratio is from about 0.05:1 to about 2.75:1.

In addition, the layered catalyst for use in the process of this invention has a critical concentration of the platinum group metal in the outer layer. This concentration is generally from about 0.026 to about 0.26 gram-mole of the platinum group metal, on an elemental basis per kilogram of the outer layer. When the platinum group metal is platinum, this concentration is from about 0.5 to about 5 wt-% of platinum on an elemental basis and based on the weight of the outer layer. For a given concentration of the platinum group metal in the outer layer, there is a preferred atomic ratio of the platinum group metal to the promoter metal. For example, when the platinum concentration is between about 0.5 and about 3 wt-% of platinum on an elemental basis and based on the weight of the outer layer, the preferred atomic ratio of platinum to tin is from between about 0.6:1 to about 1.3:1, increasing as the platinum concentration increases.

Suitable catalysts generally have a loading of the platinum group metal of from about 5 to about 30 gram-mole of the platinum group metal on an elemental basis per cubic meter of the layered catalyst. When the platinum group metal is platinum, this loading is from about 0.0010 to about 0.0060 gram of platinum on an elemental basis per cubic centimeter of catalyst.

The concentration of the platinum-group metal in the outer layer can be readily determined in at least three ways. First, the concentration can be computed based on the weight of the ingredients used in preparing the layered catalyst. Second, in the case where the layered catalyst has previously been prepared and the inner refractory inorganic oxide is different from the outer refractory inorganic oxide, then the inner layer refractory inorganic oxide can be separated from the outer refractory inorganic oxide, and the platinum group metal can be separately recovered, by known chemical and/or mechanical methods. Then, the concentration of the weight of the platinum group metal can be determined from the weight of recovered platinum group metal and the weight of recovered inner refractory inorganic oxide. Finally, energy dispersive x-ray spectroscopy or wavelength dispersive spectroscopy (EPMA) using a scanning electron microscope of a sample of the layered catalyst may also be used.

Having obtained the layered catalyst, it can be used in a hydrocarbon dehydrogenation process. It is critical that the process of this invention be carried out at certain conditions in order to achieve the surprising benefit of improved catalyst stability.

Dehydrogenatable hydrocarbons are contacted with the catalyst of the instant invention in a dehydrogenation zone maintained at dehydrogenation conditions. This contacting can be accomplished in a fixed catalyst bed system, a moving catalyst bed system, a fluidized bed system, etc., or in a batch-type operation. A fixed bed system is preferred. In this fixed bed system the hydrocarbon feed stream is preheated to the desired reaction temperature and then flowed into the dehydrogenation zone containing a fixed bed of the catalyst. The dehydrogenation zone may itself comprise one or more separate reaction zones with heating means there between to ensure that the desired reaction temperature can be maintained at the entrance to each reaction zone. The hydrocarbon may be contacted with the catalyst bed in either upward, downward or radial flow fashion. Radial flow of the hydrocarbon through the catalyst bed is preferred. The hydrocarbon may be in the liquid phase, a mixed vapor-liquid phase or the vapor phase when it contacts the catalyst. Preferably, it is in the vapor phase.

Hydrocarbons which can be dehydrogenated include hydrocarbons with 2 to 30 or more carbon atoms including normal paraffins, isoparaffins, alkylaromatics, naphthenes and olefins. A preferred group of hydrocarbons is the group of normal paraffins with 2 to about 30 carbon atoms. Especially preferred normal paraffins are those having 9 to 16 carbon atoms. Other especially preferred paraffins are monomethyl paraffins and dimethyl paraffins having from 9 to 16 carbon atoms. Each of the aforementioned hydrocarbons may be present alone or in a mixture with one or more of any of the other aforementioned hydrocarbons.

Dehydrogenation conditions include a temperature of from about 400° C. to about 900° C., a pressure of from about 1 to about 1013 kPa and a liquid hourly space velocity (LHSV) of from about 0.1 to about 100 hr$^{-1}$. As used herein, the abbreviation 'LHSV' means liquid hourly space velocity, which is defined as the volumetric flow rate of liquid per hour divided by the catalyst volume, where the liquid volume and the catalyst volume are in the same volumetric units. Generally for paraffins, the lower the molecular weight, the higher is the temperature required for comparable conversion. The pressure in the dehydrogenation zone is maintained as low as practicable, consistent with equipment limitations, to maximize the chemical equilibrium advantages.

The effluent stream from the dehydrogenation zone generally will contain unconverted dehydrogenatable hydrocarbons, hydrogen and the products of dehydrogenation reactions. This effluent stream is typically cooled and passed to a hydrogen separation zone to separate a hydrogen-rich vapor phase from a hydrocarbon-rich liquid phase. Generally, the hydrocarbon-rich liquid phase is further separated by means of either a suitable selective adsorbent, a selective solvent, a selective reaction or reactions or by means of a suitable fractionation scheme. Unconverted dehydrogenatable hydrocarbons are recovered and may be recycled to the dehydrogenation zone. Products of the dehydrogenation reactions are recovered as final products or as intermediate products in the preparation of other compounds.

The dehydrogenatable hydrocarbons may be admixed with a diluent material before, while or after being flowed to the dehydrogenation zone. The diluent material may be hydrogen, steam, methane, ethane, carbon dioxide, nitrogen, argon and the like or a mixture thereof. Hydrogen is the preferred diluent. Ordinarily, when hydrogen is utilized as the diluent it is utilized in amounts sufficient to ensure a hydrogen to hydrocarbon mole ratio of about 0.1:1 to about 40:1, with best results being obtained when the mole ratio range is about 1:1 to about 10:1. The diluent hydrogen stream passed to the dehydrogenation zone will typically be recycled hydrogen separated from the effluent from the dehydrogenation zone in the hydrogen separation zone.

Water or a material which decomposes at dehydrogenation conditions to form water such as an alcohol, aldehyde, ether or ketone, for example, may be added to the dehydrogenation zone, either continuously or intermittently, in an amount to provide, calculated on the basis of equivalent water, less than about 1000 weight ppm of the hydrocarbon feed stream, preferably less than 300 weight ppm, more preferably less than 60 weight ppm, and possibly even less than 1 weight ppm. The process of this invention may be operated with no water or material which decomposes to form water added to the dehydrogenation zone.

The following examples are presented in illustration of this invention and are not intended as undue limitations on the generally broad scope of the invention as set out in the appended claims.

EXAMPLE 1

A catalyst was prepared essentially according to the method described in Example 1 of U.S. application Ser. No. 09/887,229, except on a different scale.

Alumina spheres were prepared by the well-known oil drop method, which is described in U.S. Pat. No. 2,620,314 which is incorporated by reference. This process involves forming an aluminum hydrosol by dissolving aluminum in hydrochloric acid. Hexamethylene tetraamine was added to the sol to gel the sol into spheres when dispersed as droplets into an oil bath maintained at about 93° C. The droplets remained in the oil bath until they set and formed hydrogel spheres. After the spheres were removed from the hot oil, they were pressure-aged at about 135° C. and washed with dilute ammonium hydroxide solution, dried at about 110° C. and calcined at about 650° C. for about 2 hours to give gamma alumina spheres. The calcined alumina was then crushed into a fine powder having a particle size of less than 200 microns.

Next, a slurry was prepared by mixing aluminum sol (15 wt-% $Al_2O_3$) and deionized water and agitated to uniformly distribute the tin component. To this mixture there were added the above prepared alumina powder and a 50% aqueous solution of tin(IV) chloride, and the slurry was ball milled for approximately 240 minutes thereby reducing the maximum particle size to less than 50 microns. This slurry was sprayed onto cordierite cores having an average diameter of about 1.8 mm by using a granulating and coating apparatus to give an outer layer of about 120 microns. At the end of the process, some of the slurry was left which did not coat the cores. This layered spherical support was dried at about 200° C. and then calcined at about 600° C. in order to convert the pseudoboehmite in the outer layer into gamma alumina and convert the tin chloride to tin oxide.

The calcined layered support was impregnated with lithium and platinum using a rotary impregnator by contacting the support with an aqueous solution (1:1 solution:support volume ratio) containing lithium chloride and chloroplatinic acid based on support weight. The impregnated composite was heated using a rotary impregnator until no solution remained, dried at about 315° C. and calcined at about 540° C. and reduced in hydrogen at about 500° C.

The resulting catalyst prepared in this example contained 0.158 wt-% platinum, 0.15 wt-% tin, and 0.22 wt-% lithium with respect to the entire catalyst. This catalyst was identified as catalyst A. The properties of catalyst A are summarized in Table 1. The tin concentration in the layer was computed from the tin content of the slurry. The platinum concentration in the layer was computed by multiplying the tin concentration in the layer by the weight ratio of platinum to tin with respect to the entire catalyst.

EXAMPLE 2

A catalyst was prepared essentially according to the method described in Example 2 of U.S. application Ser. No. 09/887,229, except on a different scale. The impregnated composite was dried at 315° C. and calcined at 540° C. The resulting catalyst prepared in this example had a layer thickness of about 55 micron, and contained 0.553 wt-% platinum, 0.32 wt-% tin and 0.14 wt-% lithium. This catalyst was identified as catalyst B. The properties of catalyst B are summarized in Table 1.

TABLE 1

| Catalyst Identification | A | B |
|---|---|---|
| Core | Cordierite | Cordierite |
| Core Diameter (in) | 0.0673 | 0.0618 |
| Layer Thickness (micron) | 120 | 55 |
| Tin Concentration in Layer (wt-% tin) | 0.65 | 1.97 |
| Platinum Concentration in Layer (wt-% platinum) | 0.68 | 3.4 |
| Platinum Concentration in Layer (g-mole platinum per kilogram layer) | 0.035 | 0.17 |
| Platinum Loading (g platinum per 10 cc catalyst) | 0.012 | 0.043 |
| Platinum Loading (g-mole platinum per cubic meter catalyst) | 6.1 | 22.0 |
| Atomic Ratio of Platinum to Tin | 0.64 | 1.05 |

EXAMPLE 3

Catalyst B was tested for dehydrogenation activity in a laboratory scale plant. In a 1.27 cm (½") reactor, 10 cc of catalyst was placed and a hydrocarbon feed composed of 8.8–9.3 wt-% $n-C_{10}$, 40.0–41.8 wt-% $n-C_{11}$, 38.6 wt-% $n-C_{12}$, 8.6–10.8 wt-% $n-C_{13}$, 0.3–0.8 wt-% $n-C_{14}$ and 1–1.4 wt-% non-normals was flowed over the catalyst under a pressure of 138 kPa(g) (20 psi(g)), a $H_2$:hydrocarbon molar ratio of 6:1, and a liquid hourly space velocity (LHSV) of 20 $hr^{-1}$. The total normal olefin concentration in the product (% TNO) was maintained at 15 wt-% by adjusting reactor temperature.

Recycle hydrogen and hydrocarbon feed were combined upstream of the reactor to form a combined feed, and the combined feed was vaporized prior to entering the reactor. In this example, the catalyst was tested at water concentrations of 2000, 300, and 40–60 wt-ppm based on the weight of the hydrocarbon in the combined feed. In order to achieve the desired water concentration of 2000 wt-ppm the recycle hydrogen was routed through a water bath, and the temperature and pressure of the water were set as needed. In order to achieve the desired water concentrations of 40–60 and 300 wt-ppm an alcohol that readily decomposes at dehydrogenation conditions was injected into the combined feed. If the water concentration of the recycle hydrogen or hydrocarbon feed was too high to achieve any of these water concentrations, the recycle hydrogen or hydrocarbon feed was dried by routing through a molecular sieve. The results of the testing are presented in the Table 2 below. What is presented is the deactivation rate (slope) which is obtained by plotting temperature (° F.) needed to maintain 15% TNO (total normal olefins) versus time. The data show a substantial decrease in catalyst deactivation rate when operating at water levels of 300 wt-ppm or below.

EXAMPLE 4

Catalyst A was tested in the manner described in Example 3 at water concentrations of 2000 and 60 wt-ppm based on the weight of the hydrocarbon in the combined feed. The results are shown in the Table 2 below. Catalyst A also shows a significant decrease in deactivation rate when operating at a water level of 60 wt-ppm. However this benefit is not as substantial as the benefit seen in Example 3.

EXAMPLE 5

Catalyst A was tested in the manner described in Example 3, but with modified operating conditions. While the liquid hourly space velocity (LHSV) remained 20 hr$^{-1}$, the H$_2$:hydrocarbon molar ratio was dropped to 4:1. Water concentrations of 3000 and 1000 wt-ppm based on the hydrocarbon in the combined feed were tested. These water concentrations were achieved by routing the recycle hydrogen through a water bath and controlling the temperature and pressure of the bath. The results are shown in the Table 2 below.

EXAMPLE 6

Catalyst A was tested in the manner described in Example 5, but with a liquid hourly space velocity (LHSV) of 30 hr$^{-1}$ and a H$_2$:hydrocarbon molar ratio of 8:1. The results are shown in the Table 2 below.

In both Examples 5 and 6, the deactivation rate at 3000 wt-ppm was similar to that at 1000 wt-ppm. This implies that there is little or no change in catalyst stability between 3000 and 1000 wt-ppm water concentration. It is only below 1000 wt-ppm that an improvement in catalyst stability (a decrease in deactivation rate) is seen.

TABLE 2

| Example | Catalyst | LHSV (hr$^{-1}$) | Hydrogen/ Hydrocarbon Ratio (mol/mol) | Water Concentration (wt-ppm) | Deactivation Rate (° F./hr) |
|---|---|---|---|---|---|
| 3 | B | 20 | 6 | 2000 | 0.092 |
|   |   |    |   | 300  | 0.018 |
|   |   |    |   | 40–60 | 0.016 |
| 4 | A | 20 | 6 | 2000 | 0.096 |
|   |   |    |   | 60   | 0.05 |
| 5 | A | 20 | 4 | 3000 | 0.212 |
|   |   |    |   | 1000 | 0.198 |
| 6 | A | 30 | 8 | 3000 | 0.132 |
|   |   |    |   | 1000 | 0.142 |

What is claimed is:

1. A hydrocarbon dehydrogenation process comprising contacting a hydrocarbon stream with a layered composition under dehydrogenation conditions to give a dehydrogenated product, the layered composition comprising an inner core, an outer layer bonded to the inner core, the outer layer comprising an outer refractory inorganic oxide and having a thickness of from about 40 to about 150 microns and having uniformly dispersed thereon at least one platinum group metal and at least one promoter metal and having a concentration of the at least one platinum group metal of from about 0.026 to about 0.26 gram-mole of the platinum group metal on an elemental basis per kilogram of the outer layer, the layered composition further having dispersed thereon at least one modifier metal, the inner core and the outer refractory inorganic oxide being different materials, the layered composition further having a loading of the at least one platinum group metal of from about 5 to about 30 gram-mole of the platinum group metal on an elemental basis per cubic meter of the layered composition, the dehydrogenation conditions comprising a weight of water passed to the layered composition of less than 1000 ppm based on the hydrocarbon weight passed to the layered composition.

2. The process of claim 1 wherein the weight of water passed to the layered composition is less than 300 ppm.

3. The process of claim 1 wherein the weight of water passed to the layered composition is less than 60 ppm.

4. The process of claim 1 further characterized in that the dehydrogenation conditions comprise a temperature of about 400 to about 900° C. and a pressure of about 1 to about 1013 kPa.

5. The process of claim 1 wherein the inner core is selected from the group consisting of alpha alumina, metals, theta alumina, silicon carbide, cordierite, zirconia, titania and mixtures thereof.

6. The process of claim 1 wherein the outer refractory inorganic oxide is selected from the group consisting of gamma alumina, delta alumina, theta alumina, silica/alumina, zeolites, nonzeolitic molecular sieves, titania, zirconia and mixtures thereof.

7. The process of claim 1 wherein the platinum group metal is selected from the group consisting of platinum, palladium, rhodium, iridium, ruthenium, osmium and mixtures thereof.

8. The process of claim 1 wherein the promoter metal is selected from the group consisting of tin, germanium, rhenium, gallium, bismuth, lead, indium, cerium, zinc and mixtures thereof.

9. The process of claim 1 wherein the modifier metal is selected from the group consisting of alkali metals, alkaline earth metals and mixtures thereof.

10. The process of claim 1 wherein the hydrocarbon stream comprises at least one C$_2$–C$_{30}$ hydrocarbon selected from the group consisting of normal paraffins, isoparaffins, alkylaromatics, naphthenes, and olefins.

11. The process of claim 1 wherein the hydrocarbon stream comprises normal paraffins having 2 to 15 carbon atoms.

12. The process of claim 1 wherein the hydrocarbon stream comprises monomethyl paraffins or dimethyl paraffins.

13. A hydrocarbon dehydrogenation process comprising contacting a hydrocarbon stream with a layered composition under dehydrogenation conditions to give a dehydrogenated product, the layered composition comprising an inner core, an outer layer bonded to the inner core, the outer layer comprising an outer refractory inorganic oxide and having a thickness of from about 40 to about 150 microns and having uniformly dispersed thereon platinum and tin and having a concentration of platinum of from about 0.5 to about 5 wt-% of platinum on an elemental basis and based on the weight of the outer layer, the layered composition further having dispersed thereon lithium, the inner core and the outer refractory inorganic oxide being different materials, the layered composition further having a loading of platinum metal of from about 0.0010 to about 0.0060 gram of platinum on an elemental basis per cubic centimeter of the layered composition, the dehydrogenation conditions comprising a weight of water passed to the layered composition of less than 1000 ppm based on the hydrocarbon weight passed to the layered composition.

14. The process of claim 13 wherein the weight of water passed to the layered composition is less than 300 ppm.

15. The process of claim 13 further characterized in that the dehydrogenation conditions comprise a temperature of about 400° C. to about 900° C. and a pressure of about 1 kPa to about 1013 kPa.

16. The process of claim 13 wherein the inner core is selected from the group consisting of alpha alumina, metals, theta alumina, silicon carbide, cordierite, zirconia, titania and mixtures thereof.

17. The process of claim 13 wherein the outer refractory inorganic oxide is selected from the group consisting of gamma alumina, delta alumina, theta alumina, silica/alumina, zeolites, nonzeolitic molecular sieves, titania, zirconia and mixtures thereof.

18. The process of claim 13 wherein the hydrocarbon stream comprises a C$_9$–C$_{15}$ hydrocarbon selected from the group consisting of normal paraffins, monomethyl paraffins, and dimethyl paraffins.

* * * * *